(12) United States Patent
Bradley

(10) Patent No.: US 6,233,762 B1
(45) Date of Patent: May 22, 2001

(54) METHOD AND DEVICE TO PREVENT BED SOILING

(76) Inventor: Nanette S. Bradley, 5967 Heather View, San Antonio, TX (US) 78249

( * ) Notice: Subject to any disclaimer, the term of this patent is extended or adjusted under 35 U.S.C. 154(b) by 0 days.

(21) Appl. No.: 09/420,736

(22) Filed: Oct. 20, 1999

(51) Int. Cl.[7] .............................. A47G 9/04; A61G 9/00; A61F 13/15
(52) U.S. Cl. ........................ 5/484; 5/498; 5/500
(58) Field of Search ............................. 5/482, 484, 496, 5/498, 499, 500, 501, 502

(56) References Cited

U.S. PATENT DOCUMENTS

| 2,414,927 | * | 1/1947 | Chapman | 5/484 |
| 2,779,035 | * | 1/1957 | McMurry | 5/484 |
| 3,066,321 | * | 12/1962 | Kintner | 5/498 |
| 3,113,326 | * | 12/1963 | Hyde et al. | 5/500 X |
| 3,286,284 | * | 11/1966 | Klogether et al. | 5/484 X |
| 3,407,414 | * | 10/1968 | Burns et al. | 5/500 X |
| 3,646,624 | * | 3/1972 | Zipf, III | 5/484 |
| 3,763,907 | * | 10/1973 | Hockley et al. | 5/484 X |
| 3,849,813 | * | 11/1974 | Neilson | 5/482 X |
| 4,021,870 | * | 5/1977 | Walters | 5/484 |
| 4,064,577 | * | 12/1977 | Walters | 5/484 |
| 4,391,010 | * | 7/1983 | Kronman | 5/484 |
| 4,499,131 | * | 2/1985 | Knox | 5/484 X |
| 4,506,398 | * | 3/1985 | Hruban | 5/498 X |
| 4,524,474 | * | 6/1985 | Svensson | 5/484 |
| 4,599,756 | * | 7/1986 | Koffler | 5/484 |
| 4,627,122 | * | 12/1986 | Hopp | 5/484 |
| 4,922,565 | * | 5/1990 | Blake | 5/484 |
| 5,086,530 | * | 2/1992 | Blake | 5/484 |
| 5,092,010 | * | 3/1992 | Wong | 5/502 X |
| 5,221,273 | * | 6/1993 | Graham | 5/500 X |
| 5,327,595 | * | 7/1994 | Allen | 5/496 X |
| 5,701,617 | * | 12/1997 | Colby | 5/484 |
| 5,787,523 | * | 8/1998 | Lindberg | 5/484 X |

FOREIGN PATENT DOCUMENTS

2235132 * 2/1991 (GB) ........................ 5/484

* cited by examiner

Primary Examiner—Michael F. Trettel
Assistant Examiner—Robert G. Santos

(57) ABSTRACT

A device and a method to prevent bed sheet, mattress, or bed soiling by body fluid. The device contains a waterproof panel removably attached to a panel anchor. Two tuck panels, one attached to either side of the panel anchor, are used to stabilize the stain prevention device, preventing it from being moved around on the bed. The tuck panels are tucked underneath the mattress to stabilize the stain prevention device.

10 Claims, 2 Drawing Sheets

METHOD AND DEVICE TO PREVENT BED SOILING

BACKGROUND OF THE INVENTION

1. Field of the Invention

Applicant's invention relates to methods and devices to prevent bed soiling. More specifically, Applicant's invention is a waterproof device removably attached to a bed to block body fluid and prevent the fluid from reaching the lower bed sheet and the mattress.

2. Background Information

It is well known certain types of stains, such as blood or urine stains, are difficult to remove. The cleaning job becomes even more difficult if the stained article is large and heavy, such as a mattress. However, bed sheets and mattresses often do become stained if the person resting on the bed is incontinent; if a child sleeping on the bed is prone to bed wetting; or, if the person is a woman, the person is menstruating. Yet it is impractical and too expensive to simply throw away a stained mattress. Further, it is also not economically practical to throw away a set of bed sheets or mattress pad covers every time they become stained.

Since it is impossible or impractical to remove stains by throwing away the bed sheets, the mattress, or the mattress pad cover, an alternate solution is to prevent the lower bed sheet or mattress from becoming stained in the first place. For example, hospitals generally prevent body fluid from reaching the mattress by simply enclosing the entire mattress in a plastic cover and foregoing the mattress pad cover. However, this plastic cover makes the bed extremely hot and uncomfortable to lie on. Further, while plastic covers may prevent mattresses from becoming stained, they do not prevent bed sheets from being stained. Therefore, while hospitals no longer have to replace stained mattresses, they often do have to replace stained sheets. Finally, the plastic covers make it very difficult for the bed sheets to stay securely tucked underneath the mattress. Thus, in addition to being hot and uncomfortable, a hospital patient often has to lie in a bed where the bed sheet covers only half the bed.

Of course, bed sheet and mattress staining do not only occur in hospitals. Children wet beds, people experience incontinence, and women menstruate—all of which may stain bed sheets and mattresses—outside of hospitals. A common way to prevent bed sheet and mattress staining at home is to simply place additional bedding material on the bed, in areas where staining is likely to occur. However, because this bedding material is not secured into place, it tends to bunch up as a person tosses and turns in his or her sleep. Further, bulky bedding material placed on top of bed sheets is uncomfortable. Thus, a person who is incontinent or is menstruating must either risk staining an expensive mattress or expensive bed sheets or endure a relatively thick layer of uncomfortable, additional bedding material in areas where staining is likely to occur.

SUMMARY OF THE INVENTION

It is an object of the present invention to provide a novel device and method that can prevent body fluid from soiling bed sheets or mattresses.

It is another object of the present invention to provide a device that is breathable and comfortable to lie on while preventing body fluid from soiling bed sheets or mattresses.

It is another object of the present invention to provide a device that can be secured in place while preventing body fluid from soiling bed sheets or mattresses.

It is another object of the present invention to provide a device that only covers the area on the bed sheet or mattress that is likely to be soiled by body fluid.

It is another object of the present invention to provide a device that can be easily removed and replaced once it is soiled by body fluid.

It is another object of the present invention to provide a device that can be easily cleaned once soiled by body fluid.

It is another object of the present invention to provide a device and method to prolong the sheet life of bed sheets by having to wash them less requently.

It is another object of the present invention to provide a device that is both decorative and able to prevent body fluid from soiling the bed sheet or mattress.

In satisfaction of these and related objectives, Applicant's present invention provides a stain prevention apparatus that can be secured to a portion of a bed that is most likely to be stained by body fluid. This stain prevention apparatus is generally comprised of a waterproof panel, a panel anchor, and two tuck panels. In the preferred embodiment of the present invention, the waterproof panel is a generally rectangular bedding having an upper layer and a lower layer made of cloth, with a waterproof layer secured to and sandwiched between the upper layer and the lower layer. The waterproof panel is removably attached to a panel anchor. The panel anchor is made of cloth and is of the same general dimensions as the waterproof panel. Two tuck panels, one attached to each side of the panel anchor, are used to secure the stain prevention apparatus to the mattress.

To practice Applicant's invention, a practitioner first tucks both tuck panels underneath the mattress while making sure the area covered by the stain prevention apparatus is in the same general area where the person lying on the bed is most likely to soil the bed sheet or mattress. The waterproof panel can be attached to the panel anchor either before or after the panel tucking step. Thereafter, the person lies on the bed. After the stain prevention apparatus has been soiled, the practitioner removes the waterproof panel from the panel anchor. The waterproof panel is then washed. A replacement waterproof panel without stains can be attached to the panel anchor while the first waterproof panel is being cleaned.

DETAILED DESCRIPTION OF THE PREFERRED EMBODIMENT

Figure 1:
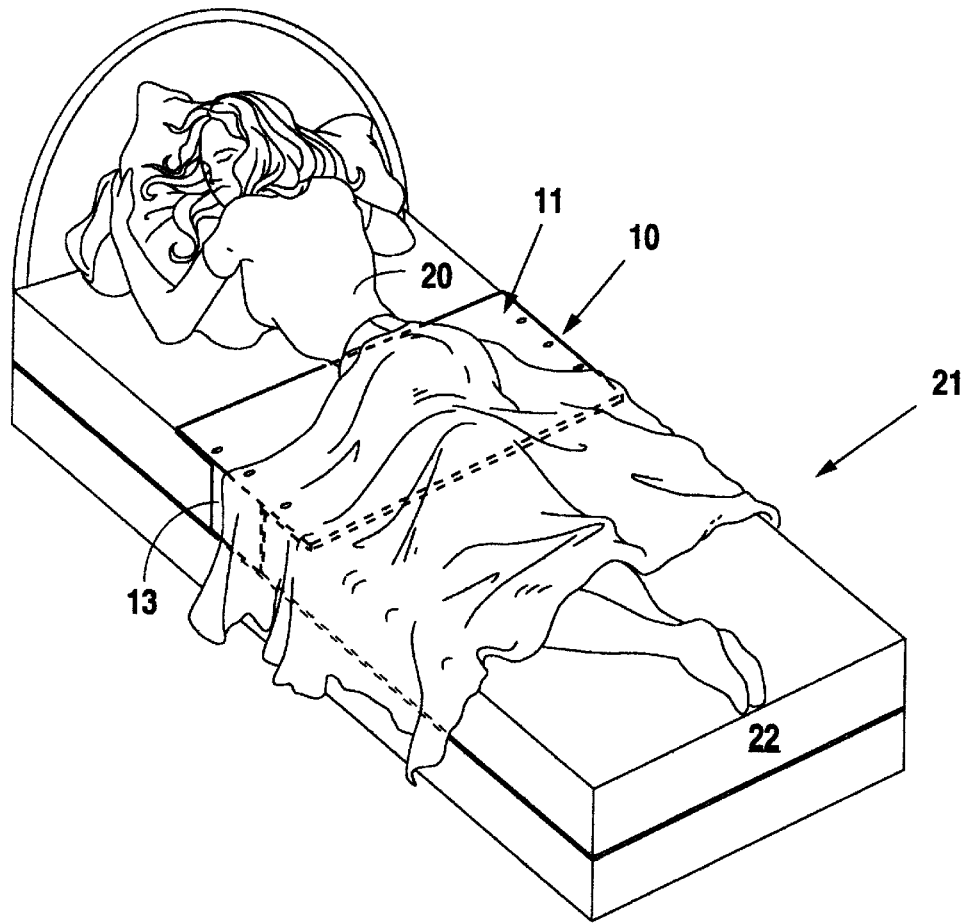
FIG. 1 is an environmental perspective view of the preferred embodiment of the stain prevention apparatus.

FIG. 1 shows a preferred embodiment of a stain prevention apparatus 10 being used by a practitioner 20. Stain prevention apparatus 10 generally consists of a waterproof panel 11, a panel anchor 12 (shown in FIG. 2), a first tuck panel 13, and a second tuck panel 14 (shown in FIG. 2). Waterproof panel 11 is removably attached to the top of panel anchor 12 (shown in FIG. 2). First and second tuck panels 13 and 14 (shown in FIG. 2) are attached to panel anchor 12.

To practice the present invention, stain prevention apparatus 10 is spread along the width of a bed 21, in an area where bed 21 is most likely to be stained. While FIG. 1 shows first and second tuck panels 13 and 14 (shown in FIG. 2) tucked underneath a mattress 22, as will be discussed below, the present invention may be practiced without tucking first and second tuck panels 13 and 14 underneath mattress 22. After securing stain prevention apparatus 10 to bed 21, practitioner 20 simply lies on top of stain prevention apparatus 10. When stain prevention apparatus 10 is stained, either the entire stain prevention apparatus 10 or only waterproof panel 11 may be removed for cleaning.

Figure 2:
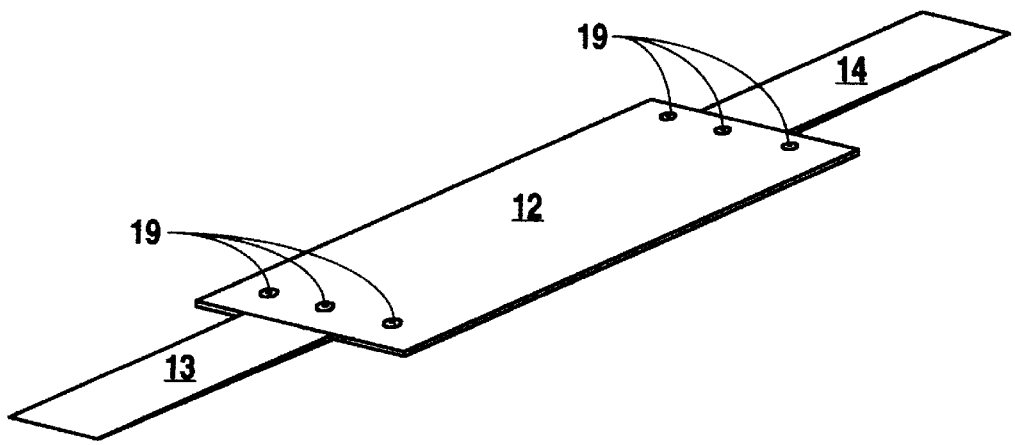
FIG. 2 is a perspective view of the anchor panel and tuck panels.

FIG. 2 shows a perspective view of panel anchor 12 and first and second tuck panels 13 and 14. Panel anchor 12 is a generally rectangular piece of material, at least one layer in thickness. In the preferred embodiment, panel anchor 12 is made of cloth. However, panel anchor 12 maybe made of any pliable material. A plurality of buttons 19 are located along the two shorter sides of panel anchor 12. Buttons 19 are used to secure waterproof panel 11 to panel anchor 12 (See FIG. 4). While buttons 19 are shown in the preferred embodiment of the present invention, it should be noted that any type of fasteners available in the marketplace such as Velcro® brand fasteners or zippers may be used to attach waterproof panel 11 to panel anchor 12.

FIG. 2 also shows first tuck panel 13 and second tuck panel 14 attached to panel anchor 12 along the width of panel anchor 12. While, in the preferred embodiment, first and second tuck panels 13 and 14 are generally rectangular in shape, first and second tuck panels 13 and 14 can be of any shape and size as long as a portion of first and second tuck panels 13 and 14 can be tucked underneath mattress 22 to stabilize stain prevention apparatus 10. In the preferred embodiment, first and second tuck panels 13 and 14 are made of cloth. However, first and second tuck panel 13 and 14 can be made of any flexible material of any thickness strong enough to prevent stain prevention apparatus 10 from being displaced on bed 21.

First and second tuck panels 13 and 14 may be removably attached to panel anchor 12. The ability to detach first and second tuck panels 13 and 14 from panel anchor 12 allows panel anchor 12 to be washed separately from first and second tuck panels 13 and 14. The removability of first and second tuck panels 13 and 14 from panel anchor 12 prevents first and second tuck panels 13 and 14 from being worn by repeated and unnecessary washing.

In an alternate embodiment, a plurality of small weights (not shown) may be attached or sewn into first and second tuck panels 13 and 14 for additional weight at their respective ends farther from panel anchor 12. With the weights, practitioner 20 may choose not to tuck first and second tuck panels 13 and 14 underneath mattress 22 and instead use only the weights to keep stain prevention apparatus 10 from being displaced.

Alternate embodiments of the present invention (not shown) may further include additional small weights attached or sewn into the edges of panel anchor 12, near buttons 19. These additional small weights will serve as additional means to stabilize and prevent stain prevention apparatus 10 from being moved around bed 21.

Figure 3:
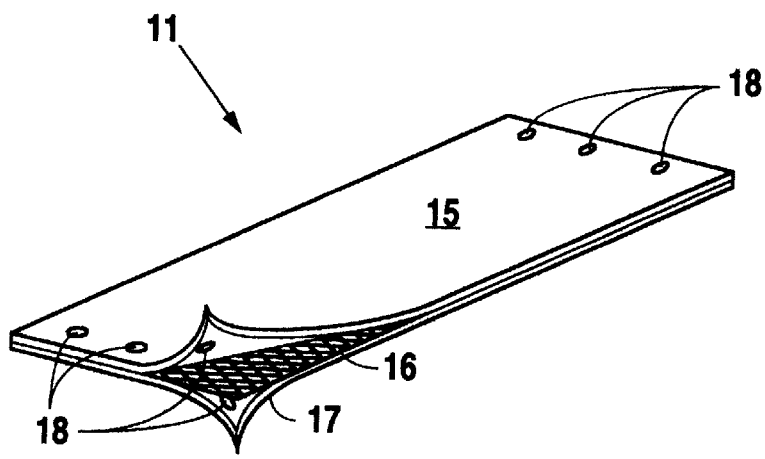
FIG. 3 is a perspective view of the waterproof panel.

FIG. 3 shows waterproof panel 11 as detached from panel anchor 12. In the preferred embodiment, waterproof panel 11 is generally rectangular and generally consists of an upper layer 15, a waterproof layer 16, and a lower layer 17. Waterproof layer 16 is sandwiched and secured between upper layer 15 and lower layer 17. Upper layer 15 and lower layer 17 can be made of any soft, water permeable, breathable, and fluid absorbent material such as cloth. Waterproof layer 16 can be made of any waterproof and preferably washable material available in the marketplace. However, waterproof layer 16 must be made of a pliable material so a person lying on waterproof panel 11 will not experience discomfort caused by the stiffness of waterproof layer 16.

A plurality of buttonholes 18 are placed along both sides of waterproof panel 11. Buttonholes 18 are used to attach waterproof panel 11 to panel anchor 12. While buttonholes 18 are used in the preferred embodiment, it should be noted any method of removably attaching one object to another may be used to attach waterproof panel 11 to panel anchor 12.

While waterproof panel 11 may be of any size or shape, in the preferred embodiment, waterproof panel 11 is rectangular in shape. Finally, waterproof panel 11 may be decorated with various types of indicia for aesthetic purposes.

Figure 4:
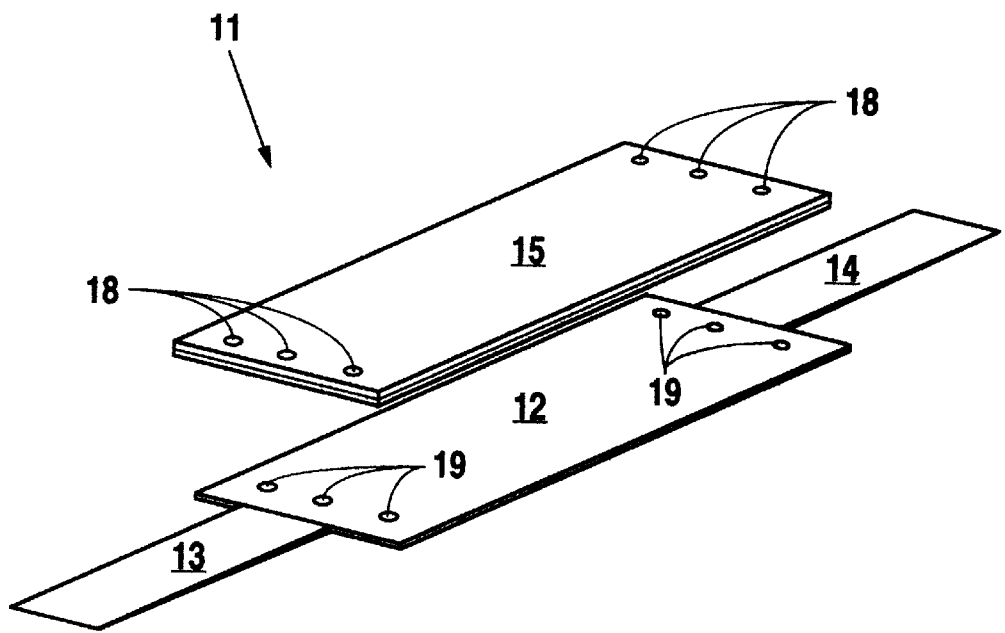
FIG. 4 is an exploded perspective view of the present invention.

FIG. 4 shows a perspective view of stain prevention apparatus 10 just prior to waterproof panel 11 being attached to panel anchor 12. Waterproof panel 11 is removably attached directly on top of panel anchor 12 by using attaching devices such as buttons 19 and buttonholes 18.

To practice the present invention, practitioner 20 first spreads stain prevention apparatus 10 along the width of her bed, on an area likely to be stained. Tuck panels 13 and 14 may be tucked underneath mattress 22. She then lies on the bed, on top of stain prevention apparatus 10. (See FIG. 1.) After stain prevention apparatus 10 is soiled, practitioner 20 simply detaches waterproof panel 11 from panel anchor 12 and washes waterproof panel 11. Because of waterproof layer 16, the body fluid, while soiling upper layer 15, will not reach lower layer 17. Body fluid will also not reach panel anchor 12. Therefore, panel anchor 12 will not need to be cleaned. Instead, panel anchor 12 may be left on the bed and a clean replacement waterproof panel 11 may be immediately attached to panel anchor 12. Alternatively, the entire stain prevention apparatus 10 may be removed and cleaned after waterproof panel 11 is soiled.

Although the invention has been described with reference to specific embodiments, this description is not meant to be construed in a limited sense. Various modifications of the disclosed embodiments, as well as alternative embodiments of the inventions, will become apparent to persons skilled in the art upon the reference to the description of the invention. It is, therefore, contemplated that the appended claims will cover such modifications that fall within the scope of the invention.

I claim:

1. A device for preventing bed sheet or mattress staining by a person lying thereon, comprising:

a rectangular waterproof panel having two opposite long sides and two opposite short side for extending across said mattress on said bed sheet and placed below a mid-portion of said person, said waterproof panel having a liquid permeable and comfortable top layer for contact with said mid-portion of said person and a waterproof layer attached generally underneath said top layer for preventing body fluid from penetrating said waterproof layer;

a rectangular anchor panel of approximately the same size as said waterproof panel and having two opposite long sides two opposite short sides, and fasteners disposed along the short sides for removably attaching said waterproof panel to said anchor panel, said anchor panel disposed generally below said waterproof panel; and at least two rectangular tuck panels, each said tuck panel having two opposite long sides and two opposite short sides respectively smaller than said long and short sides of said anchor panel and attached along a short side thereof to opposite short sides of said anchor panel and adapted to secure said waterproof panel and said anchor panel in place on said mattress underneath said midportion of said person.

2. A device for preventing bed sheet or mattress staining as in claim 1 wherein said top layer is made of cloth.

3. A device for preventing bed sheet or mattress staining as in claim 1 wherein said top layer and said waterproof layer are attached to a bottom layer disposed underneath said waterproof layer.

4. A device for preventing bed sheet or mattress staining as in claim 1 wherein said tuck panels are adapted to secure said waterproof panel and said anchor panel to said mattress by being tucked underneath said mattress.

5. A device for preventing bed sheet or mattress staining as in claim 1 wherein weights are attached to each said tuck panel at ends opposite to each said tuck panel's attaching point to said anchor panel.

6. A device for preventing bed sheet or mattress staining as in claim 1 wherein weights are attached to said anchor panel near said anchor panel's attaching point to each said tuck panel.

7. A method for preventing bed sheets or mattress of a bed from staining by a person lying thereon comprising the steps:

placing a device on said bed sheets or said mattress of said bed, comprising:

a rectangular waterproof panel having two opposite long sides and two opposite short sides and a top layer made of a comfortable material and a waterproof layer attached generally below said top layer;

a rectangular anchor panel of approximately the same size as said waterproof panel having at least two opposite long sides and two opposite short sides and having fasteners disposed along the short sides for removably attaching said waterproof panel to said anchor panel; and at least two rectangular tuck panels for securing to said bed said device for preventing said bed sheet or said mattress from staining to said bed, each said tuck panel having two opposite long sides and two opposite short sides respectively smaller than said long and short sides of said anchor panel and attached along a short side to each said opposite short side of said anchor panel;

securing said tuck panels to said bed;

resting by said person on said bed; and subsequently detaching and removing said waterproof panel from said anchor panel after said waterproof panel is soiled by body fluids from said person.

8. A method for preventing staining of bed sheets or mattress of said bed as recited in claim 7 having the additional step of attaching a second waterproof panel to said anchor panel after said detaching and removing step.

9. A method for preventing staining of bed sheets or mattress of said bed as recited in claim 7 having the additional step of cleaning said waterproof panel after said detaching and removing step.

10. A method for preventing staining of bed sheets or mattress of said bed as recited in claim 7 wherein said securing step comprises tucking a portion of said tuck panels underneath said mattress.

* * * * *